United States Patent [19]

Squire et al.

[11] 4,292,437

[45] Sep. 29, 1981

[54] PREPARATION OF ISOBUTYRIC ACID AND ESTERS

[75] Inventors: Edward N. Squire, Glen Mills, Pa.; Francis J. Waller, Wilmington, Del.

[73] Assignee: E. I. Du Pont de Nemours and Company, Wilmington, Del.

[21] Appl. No.: 53,232

[22] Filed: Jun. 27, 1979

[51] Int. Cl.³ .............................................. C07C 67/38
[52] U.S. Cl. .................................. 560/233; 252/429 R
[58] Field of Search ........................ 560/233; 562/522

[56] References Cited

U.S. PATENT DOCUMENTS

| | | | |
|---|---|---|---|
| 3,102,899 | 9/1963 | Connell | 260/439 R |
| 3,168,553 | 2/1965 | Slaugh | 562/522 |
| 3,437,676 | 4/1969 | Kutepow | 560/233 |
| 3,501,518 | 3/1970 | Kutepow | 560/233 |
| 3,530,168 | 9/1970 | Biale | 560/233 |
| 3,622,607 | 11/1971 | Fenton | 562/522 |
| 3,641,074 | 2/1972 | Fenton | 560/233 |
| 3,641,076 | 2/1972 | Booth | 562/522 |
| 3,668,249 | 6/1972 | Fenton | 562/522 |
| 3,700,706 | 10/1972 | Butter | 562/522 |
| 3,723,486 | 3/1973 | Kajimato | 560/233 |
| 3,733,362 | 5/1973 | Biale | 562/522 |
| 3,755,421 | 8/1973 | Fenton | 560/233 |
| 3,793,369 | 2/1974 | Hara | 560/233 |
| 3,839,378 | 10/1974 | Yamaguchi | 560/233 |
| 3,857,900 | 12/1974 | Wilkinson | 560/233 |
| 3,859,319 | 1/1975 | Mrowca | 560/233 |
| 3,887,595 | 6/1975 | Nozaki | 560/233 |
| 3,919,272 | 11/1975 | Knifton | 560/233 |
| 3,933,919 | 1/1976 | Wilkinson | 560/233 |
| 3,968,133 | 7/1976 | Knifton | 560/233 |

FOREIGN PATENT DOCUMENTS

| | | | |
|---|---|---|---|
| 2739096 | 3/1978 | Fed. Rep. of Germany | 560/233 |
| 47-25050 | 7/1972 | Japan | 560/233 |

OTHER PUBLICATIONS

Fenton, J. Org. Chem., 38, pp. 3192–3198 (1973).
Knifton, J. Org. Chem., 41, pp. 2885–2890 (1976).
Consiglio, Chimia, 30 pp. 26–27 (1976).

*Primary Examiner*—Natalie Trousof
*Assistant Examiner*—Michael Shippan

[57] ABSTRACT

Preparation of isobutyric acid and esters by carbonylation of propylene in the presence of water or an alcohol, a palladium catalyst and ortho-substituted triarylphosphine.

5 Claims, No Drawings

PREPARATION OF ISOBUTYRIC ACID AND ESTERS

BACKGROUND OF THE INVENTION

Lower alkyl isobutyrates are widely used in industrial syntheses. For example, methyl isobutyrate can be dehydrogenated to methyl methacrylate, which is then polymerized to a polymethyl methacrylate useful in sheet form or in a variety of other molded shapes.

Lower alkyl isobutyrates are conveniently prepared by the reaction of propylene and carbon monoxide with a lower alkanol. A wide variety of catalysts has been suggested and used for this reaction, including a combination of palladous chloride and triphenyl phosphine. While this catalyst system gives a high degree of reaction of the components, the resulting product mixture is a combination of straight-chain alkyl butyrate and alkyl isobutyrate. With increasing commercial interest in the alkyl isobutyrate compositions, a need exists to maximize the percentage of the branched composition resulting from this reaction.

SUMMARY OF THE INVENTION

The instant invention provides an improved process for the preparation of lower alkyl butyrate esters which results in a substantially higher percentage of the isobutyrate products than has heretofore been realized from phosphine liganded palladium catalysts.

Specifically, the instant invention provides an improvement in the process for the carbonylation of propylene by contacting the propylene and carbon monoxide with water or a lower alkanol of 1 to 4 carbon atoms in the presence of solvent and a palladium catalyst in complex with a ligand, which improvement comprises an ortho-substituted ligand of the formula $PAr_3$ wherein each Ar is independently selected from

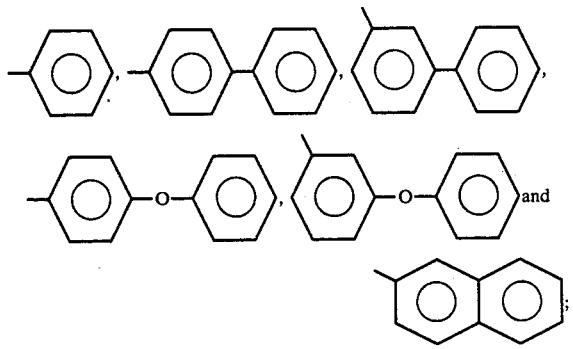

and wherein the Ar moieties bear a total of one or two substituents in positions ortho to one or two carbon-phosphorus bonds, the substituents being selected from the group consisting of lower alkyl of 1-4 carbon atoms, lower alkoxy and phenyl and wherein the Ar groups each contain up to three substituents in positions meta or para to a carbon-phosphorus bond and selected from the group consisting of lower alkyl, lower alkoxy, chloride, fluoride, hydroxyl and carboxyl.

DETAILED DESCRIPTION OF THE INVENTION

The present invention is based on the discovery of the unique suitability of certain triaryl phosphine ligands in conjunction with a palladium catalyst in the conversion of propylene into isobutyric acid or its ester in unusually high yields as opposed to the corresponding unbranched product. This unusually high yield of branched product is realized through the use of ortho-substituted triaryl phosphines in which one or two of the three aromatic moieties is substituted in a position ortho to the carbon-phosphorus bond with at least one substituent from the group consisting of lower alkyl of one to four carbon atoms, lower alkoxy and phenyl. The triaryl phosphine can have a total of one or two such ortho substituents.

The ligands used in the instant invention therefore have one or two of the required substituents in the six possible positions ortho to the three carbon atoms bearing a phosphorus bond. Two ortho substituents appear on the same or different rings, and can be the same or different substituents. In addition to the indicated lower alkyl, lower alkoxy and phenyl substituents, α-naphthyl can be used as an ortho-substituted Ar group.

In addition to the ortho substituents, the aryl groups can each be substituted with up to three substituents in the positions meta and para to the carbon-phosphorus bond and selected from the group consisting of lower alkyl, lower alkoxy, chloride, fluoride, hydroxyl, and carboxyl. However, these meta and para substitutents do not significantly effect directive properties of the ligand in producing the desired branched configuration.

The ligands can be readily prepared using conventional reaction techniques from aryl bromides or chlorides coupled with trivalent phosphorus halides, or from aryl substituted trivalent phosphorus halides through the use of sodium or magnesium.

Of the many ligands described above, those having the following chemical structures are preferred:

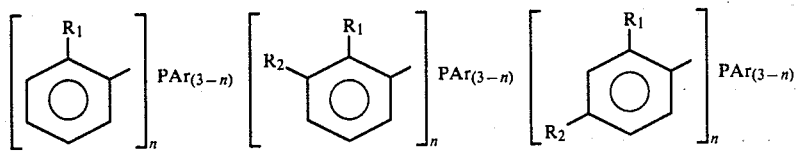

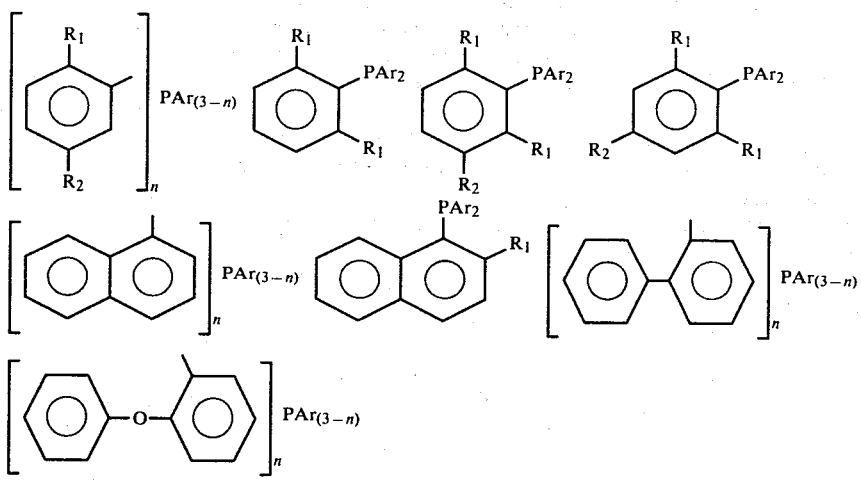

in which n=1 or 2 and wherein Ar is

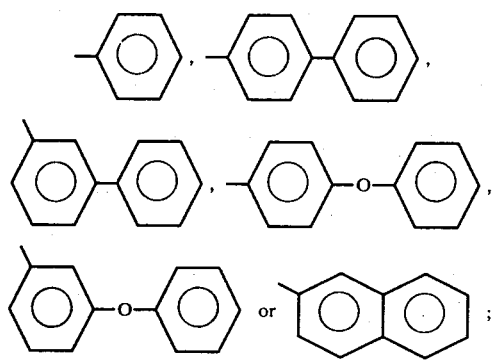

$R_1$ is selected from the group consisting of alkyl of 1-4 carbon atoms, alkoxy, and phenyl; and $R_2$ is selected from the group consisting of alkyl of 1-4 carbon atoms, alkoxy, chloride, fluoride, hydroxyl and carboxyl.

The ligands are used in conjunction with palladium. The molar ratio of the ligands to the palladium is about from 4:1 to 122:1. The palladium is usually combined with the ligand before addition to the reaction mixture or added to the reaction mixture in the form of a soluble salt such as palladium halides, sulfates, nitrates and salts of lower carboxylic acids containing up to five carbon atoms. Particularly satisfactory in the instant invention is palladium dichloride.

The reaction is performed by bringing into contact propylene, carbon monoxide, halide acid and the catalyst.

The solvents which can be used in the present process include a wide variety of organic solvents which do not interfere with the reaction and in which the aryl phosphine liganded palladium is soluble under operating conditions. These include aromatic hydrocarbons such as benzene, toluene, xylenes, naphthalene, chlorinated aromatic compounds such as chlorobenzene, dichlorobenzene, chloronaphthalenes, chlorinated aliphatic compounds such as chloroform, 1,1,2,2-tetrachloroethane, 1,1,2,2-trichloroethane, and sulfones such as diethylsulfone, tetramethylene sulfone, dipropyl sulfone, dibutyl sulfone, or organic acids such as acetic, butyric or isobutyric acid.

The carbon monoxide is most conveniently added by maintaining a carbon monoxide gas pressure in the reaction vessel of about from 1.4 to 35 mega Pascals, and preferably about from 7 to 21 mega Pascals. It has been found that the reaction rate is undesirably slow at a pressure below 1.4 mega Pascals and little additional benefit is obtained by pressures in excess of 35 mega Pascals.

An alcohol of one to four carbon atoms or water is used in the present reaction, depending on whether an ester or acid product is desired. In general, the alcohol or water is present in the range of about from $1 \times 10^{-2}$ to 1 mole of propylene per mole of alcohol or water. Preferably, about from 1.0 to 1.6 moles of alcohol or water per mole of propylene is used.

The carbonylation reaction producing high percentages of branched products is conducted in the presence of small amounts of halide acid. Such acids can include hydrogen fluoride, hydrogen chloride, hydrogen bromide and hydrogen iodide. The acid is generally present in the amount of $1 \times 10^{-3}$ to $1 \times 10^{-1}$ moles of acid per each mole of alcohol or water present. Preferably the acid is present in quantities of about from $1 \times 10^{-2}$ to $6 \times 10^{-2}$ moles of the acid per mole of alcohol or water. Hydrogen chloride is particularly preferred for use as an acid.

The amount of catalyst used in the instant process can vary widely, depending on the reaction rate desired and the particular reactants used and the metal in the catalyst. In general, the catalyst is present in amounts to provide about from 1 to $1 \times 10^{-5}$ mole of noble metal per mole of propylene in the reaction mixture. For efficiency and economy, $1 \times 10^{-2}$ to $1 \times 10^{-4}$ mole of catalyst are preferred.

The reaction is generally carried out at a temperature of about from 100° to 180° C., and preferably about from 120° to 160° C. In general, lower reaction temperatures are preferred, since greater quantities of catalysts can be recovered at these lower temperatures. The pressure of the reaction vessel is maintained at about from 200 to 6000 psi, and a pressure of 1,000 to 3,000 psi is preferred. Improved catalyst recovery is similarly obtained with lower reaction pressures.

A wide variety of reaction vessels can be used with the present invention, including those prepared from tantalum, platinum, glass, quartz, or fluorocarbon resin.

The process of the instant invention results in the economical conversion of propylene to isobutyric acid and its esters. The branched product is obtained in substantially higher proportion than has heretofore been possible using phosphine liganded catalysts. While arsine liganded catalysts can give a proportion of branched ester equivalent to the present process, acids cannot be satisfactorily made with these catalysts. The branched compound resulting from the instant invention frequently represents 80 to 90% of the total acid or ester reaction product.

The present invention is further illustrated by the following specific examples.

EXAMPLES 1-19 AND COMPARATIVE EXAMPLES A-F

In these examples, the indicated compounds were reacted in a 330 milliliter nickel-steel alloy shaker tube operated at 84 12-inch strokes per minute. The compounds were introduced in the quantities indicated in the Table and pressurized under a carbon monoxide feed. Reaction times, temperatures and pressures are as indicated in the accompanying Tables.

TABLE

| Example | Ligand | % Iso Distribution in Product |
|---|---|---|
| 1 | o-tolyl diphenylphosphine | 81 |
| A | triphenylphosphine | 47 |
| B | tris(p-tolyl) phosphine | 53 |
| 2 | o-tolyl diphenylphosphine | 92.5 |
| 3 | bis(o-tolyl) phenylphosphine | 88.7 |
| C | tris(o-tolyl) phosphine | 91.3* |
| 4 | bis(o-tolyl) phenylphosphine | 90.9 |
| 5 | o-anisyl diphenyl phosphine | 88.8 |
| 6 | o-anisyl diphenyl phosphine | 82.7 |
| 7 | bis(ortho anisyl) phenylphosphine | 92.6 |
| 8 | bis(2,4-dimethylphenyl) phenylphosphine | 92.3 |
| 9 | bis(2,5-dimethylphenyl) phenylphosphine | 92.5 |
| D | bis(3-chlorophenyl) phenylphosphine | 66.8 |
| E | bis(3,4-dimethylphenyl) phenyl phosphine | 62.4 |
| 10 | Tris(o-anisyl) phosphine | ** |
| 11 | bis(2,5-dimethyoxyphenyl) phenylphosphine | 88.2 |
| 12 | bis(o-anisyl) p-anisyl phosphine | 89.8 |
| 13 | bis(o-anisyl) 3,4-dichlorophenylphosphine | 88.6 |
| 14 | bis(o-chlorophenyl) phenylphosphine | 61.5 |
| 15 | 2,4-dimethylphenyl diphenylphosphine | 89.3 |
| 16 | bis(alpha-naphthyl) phenyl phosphine | 88.7 |
| 17 | bis(ortho fluorophenyl) phenyl phosphine | 69.5 |
| 18 | bis(2,5-dimethylphenyl) phenylphosphine | 91.0 |
| F | triphenylphosphine | 56.1 |
| 19 | bis(1-naphthyl) phenylphosphine | 89.8 |

*Ligand-Palladium compound is unstable and gives less than 1% propylene conversion.
**No significant reaction

REACTANTS

| Example | Reactant | Grams of Reactant |
|---|---|---|
| 1 | o-tolyl P($\phi$)$_2$ | 0.6 |
|   | (o-MeC$_6$H$_4$P$\phi_2$)$_2$PdCl$_2$ | 0.7 |
|   | KOAc | 1.0 |
|   | HOAc | 20 |
|   | H$_2$O | 4.5 |
|   | MeOH | 8.0 |
|   | propene | 50.4 |
|   | CHCl$_3$ | 30 |
| A | $\phi_3$P | 0.5 |
|   | ($\phi_3$P)$_2$PdCl$_2$ | 0.7 |
|   | HOAc | 20 |
|   | H$_2$O | 9 |
|   | CHCl$_3$ | 30 |
|   | propene | 50.4 |
| B | (p-tolyl)$_3$P | 0.6 |
|   | [(p-tolyl)$_3$P]$_2$PdCl$_2$ | 0.8 |
|   | HOAc | 20 |
|   | H$_2$O | 9 |
|   | CHCl$_3$ | 30 |
|   | propene | 50.4 |
| 2 | o-tolyl P$\phi_2$ | 0.6 |
|   | (o-tolyl P$\phi_2$)$_2$PdCl$_2$ | 0.35 |
|   | CHCl$_3$ | 60 |
|   | MeOH | 16 |
|   | CF$_3$COOH | 5.7 |
|   | propene | 50.4 |
| 3 | [(o-tolyl)$_2$P$\phi$]$_2$PdCl$_2$ | 1.5 |
|   | HOAc | 20 |
|   | H$_2$O | 9 |
|   | CHCl$_3$ | 30 |
|   | propene | 50.4 |
| C | (o-tolyl)$_3$P | 1.5 |
|   | [(o-tolyl)$_3$P]$_2$PdCl$_2$ | 0.4 |
|   | CHCl$_3$ | 60 |
|   | CH$_3$OH | 16 |
|   | CF$_3$COOH | 5.7 |
|   | propene | 50.4 |
| 4 | (o-tolyl)$_2$P$\phi$ | 0.6 |
|   | [(o-tolyl)$_2$P$\phi$]$_2$PdCl$_2$ | 0.35 |
|   | CHCl$_3$ | 30 |
|   | HOAc | 20 |
|   | MeOH | 12.8 |
|   | H$_2$O | 1.8 |
|   | propene | 50.4 |
| 5 | o-MeOC$_6$H$_4$P$\phi_2$ | 0.6 |
|   | (o-MeOC$_6$H$_4$P$\phi_2$)$_2$PdCl$_2$ | 0.4 |
|   | CHCl$_3$ | 60 |
|   | CF$_3$COOH | 5.7 |
|   | MeOH | 16 |
|   | propene | 50.4 |
| 6 | o-MeOC$_6$H$_4$P$\phi_2$ | 0.6 |
|   | [o-MeOC$_6$H$_4$P$\phi_2$]PdCl$_2$ | 0.4 |
|   | CHCl$_3$ | 30 |
|   | HOAc | 20 |
|   | MeOH | 12.8 |
|   | propene | 50.4 |
| 7 | (o-MeOC$_6$H$_4$)$_2$P$\phi$ | 0.64 |
|   | [(o-MeOC$_6$H$_4$)$_2$P$\phi$]$_2$PdCl$_2$ | 0.41 |
|   | CHCl$_3$ | 60 |
|   | MeOH | 16 |
|   | $\eta$-butyric acid | 1.5 |
|   | i-butyric acid | 13.5 |
|   | propene | 50.4 |
| 8 | [(2,4-Me$_2$C$_6$H$_3$)$_2$P$\phi$]$_2$PdCl$_2$ | 0.38 |
|   | (2,4-Me$_2$C$_6$H$_3$)$_2$P$\phi$ | 0.6 |
|   | CHCl$_3$ | 60 |
|   | MeOH | 16 |
|   | $\eta$-butyric acid | 1.0 |
|   | i-butyric acid | 10.0 |
|   | propene | 50.4 |
| 9 | [(2,5-Me$_2$C$_6$H$_3$)$_2$P$\phi$]$_2$PdCl$_2$ | 0.4 |
|   | (2,5-Me$_2$C$_6$H$_3$)$_2$P$\phi$ | 0.64 |
|   | CHCl$_3$ | 60 |
|   | MeOH | 16 |
|   | $\eta$-butyric acid | 0.8 |
|   | i-butyric acid | 8.0 |
|   | propene | 50.4 |
| D | [(3-ClC$_6$H$_4$)$_2$P$\phi$]$_2$PdCl$_2$ | 0.42 |
|   | [3-ClC$_6$H$_4$]$_2$P$\phi$ | 1.0 |
|   | CHCl$_3$ | 60 |
|   | MeOH | 16 |
|   | CF$_3$COOH | 5.7 |
|   | propene | 50.4 |
| E | (3,4-Me$_2$C$_6$H$_3$)P$\phi$ | 0.95 |
|   | [(3,4-Me$_2$C$_6$H$_3$)$_2$P$\phi$]$_2$PdCl$_2$ | 0.4 |
|   | CHCl$_3$ | 60 |

| | REACTANTS | |
|---|---|---|
| | MeOH | 16 |
| | CF₃COOH | 5.7 |
| | propene | 50.4 |
| 10 | (o-MeOC₆H₄)₃P | 0.7 |
| | [(o-MeOC₆H₄)₃P]₂PdCl₂ | 0.44 |
| | CHCl₃ | 60 |
| | MeOH | 16 |
| | CF₃COOH | 5.7 |
| | propene | 50.4 |
| 11 | [2,5-(MeO)₂C₆H₃]₂Pφ | 0.8 |
| | [(2,5-(MeO)₂C₆H₃)₂Pφ]₂PdCl₂ | 0.47 |
| | CHCl₃ | 60 |
| | MeOH | 16 |
| | H₂O | 5.4 |
| | propene | 50.4 |
| | LiCl | 0.13 |
| 12 | (o-MeOC₆H₄)₂P(p-MeOC₆H₄) | 0.7 |
| | [(o-MeOC₆H₄)₂P(p-MeOC₆H₄)]₂PdCl₂ | 0.44 |
| | CHCl₃ | 60 |
| | MeOH | 16 |
| | H₂O | 0.9 |
| | propene | 50.4 |
| 13 | [(o-MeOC₆H₄)₂P(3,4 Cl₂C₆H₃)] | 0.8 |
| | [(o-MeOC₆H₄)₂P(3,4 Cl₂C₆H₃)]₂PdCl₂ | 0.48 |
| | CHCl₃ | 60 |
| | MeOH | 16 |
| | H₂O | 36 |
| 14 | (o-ClC₆H₄)₂Pφ | 0.66 |
| | [(o-ClC₆H₄)₂Pφ]₂PdCl₂ | 0.42 |
| | CHCl₃ | 60 |
| | MeOH | 16 |
| | H₂O | 0.9 |
| | propene | 50.4 |
| 15 | (2,4-Me₂C₆H₃)Pφ₂ | .95 |
| | [(2,4-Me₂C₆H₃)Pφ₂]₂PdCl₂ | .46 |
| | CHCl₃ | 60 |
| | MeOH | 16 |
| | H₂O | 0.9 |
| | propene | 25.2 |
| 16 | (1-napthyl)₂Pφ | 1.1 |
| | [(1-napthyl)₂Pφ]₂PdCl₂ | 0.45 |
| | CHCl₃ | 60 |
| | MeOH | 16 |
| | H₂O | 0.9 |
| | propene | 25.2 |
| 17 | [(o-FC₆H₄)₂Pφ]₂PdCl₂ | 0.38 |
| | (o-FC₆H₄)₂Pφ | 0.9 |
| | CHCl₃ | 60 |
| | MeOH | 16 |
| | 85% H₃PO₄ | 1.2 |
| | H₂O | 0.9 |
| | propene | 25.2 |
| 18 | (2,5-Me₂C₆H₃)₂Pφ | 0.95 |
| | [(2,5-Me₂C₆H₃)₂Pφ]PdCl₂ | 0.081 |
| | Toluene | 36.8 |
| | MeOH | 12.8 |
| | Conc. HCl | 4 |
| | propene | 50.4 |
| F | Triphenylphosphine | 0.79 |
| | (φ₃P)₂PdCl₂ | 0.070 |
| | Toluene | 36.8 |
| | MeOH | 25.6 |
| | Conc. HCl | 4 ml |
| | propene | 42 |
| 19 | (1-napthyl)₂Pφ | 1.086 |
| | [(1-napthyl)₂Pφ]PdCl₂ | 0.090 |
| | CHCl₃ | 60 |
| | MeOH | 25.6 |
| | Conc. HCl | 4 ml |
| | propene | 42 |

| Example | Reaction Stage 1 | | | Reaction Stage 2 | | |
|---|---|---|---|---|---|---|
| | hours | °C. | psi | hours | °C. | psi |
| 1 | 2 | 110 | 1600 | 2 | 135 | 2500 |
| A | 2 | 110 | 1600 | 2 | 135 | 2500 |
| B | 2 | 110 | 1600 | 2 | 135 | 2500 |
| 2 | 2 | 135 | 1600 | — | — | — |
| 3 | 2 | 110 | 1600 | 2 | 135 | 2500 |
| C | 2 | 135 | 1600 | — | — | — |
| 4 | 2 | 135 | 1600 | — | — | — |
| 5 | 2 | 135 | 1600 | — | — | — |
| 6 | 2 | 135 | 1600 | — | — | — |
| 7 | 2 | 135 | 1600 | — | — | — |
| 8 | 2 | 135 | 1600 | — | — | — |
| 9 | 2 | 135 | 1600 | — | — | — |
| D | 2 | 135 | 1600 | — | — | — |
| E | 2 | 135 | 1600 | — | — | — |
| 10 | 2 | 135 | 1600 | — | — | — |
| 11 | 2 | 140 | 1600 | — | — | — |
| 12 | 4 | 140 | 1600 | — | — | — |
| 13 | 4 | 140 | 1600 | — | — | — |
| 14 | 4 | 140 | 1600 | — | — | — |
| 15 | 2 | 140 | 1600 | — | — | — |
| 16 | 2 | 140 | 1600 | — | — | — |
| 17 | 2 | 130 | 1400 | — | — | — |
| 18 | 2 | 130 | 1600 | — | — | — |
| F | 2 | 130 | 1600 | — | — | — |
| 19 | 3 | 115 | 1500 | — | — | — |

We claim:

1. In the process for the carbonylation of propylene by contacting the propylene and carbon monoxide with water or a lower alkanol of 1 to 4 carbon atoms in the presence of solvent and a palladium catalyst in complex with a ligand, the improvement which comprises using as said ligand an ortho-substituted ligand of the formula P Ar₃ wherein each Ar is independently selected from

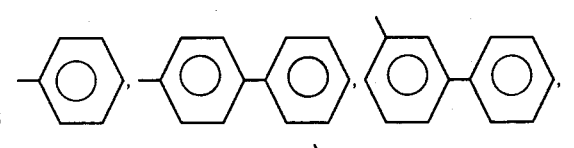

and wherein the Ar moieties bear a total of one or two substituents in positions ortho to one or two carbon-phosphorus bonds, the substituents being selected from the group consisting of lower alkyl of 1–4 carbon atoms, lower alkoxy and phenyl, and wherein the Ar groups each contain up to three substituents in positions meta or para to a carbon-phosphorus bond and selected from the group consisting of lower alkyl, lower alkoxy, chloride, fluoride, hydroxyl and carboxyl and provided that when Ar is

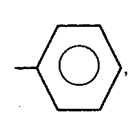

one or two of the Ar moieties can each bear one substituent selected from phenoxy and a fused aromatic hydrocarbon ring at an ortho position to form 1-naphthyl, and provided further that when the substituent is a fused aromatic hydrocarbon ring, each such Ar moiety can bear one additional substituent at a second ortho position selected from alkyl of 1-4 carbon atoms, alkoxy and phenyl.

2. A process of claim 1 wherein the ortho-substituted ligand is selected from the group consisting of:

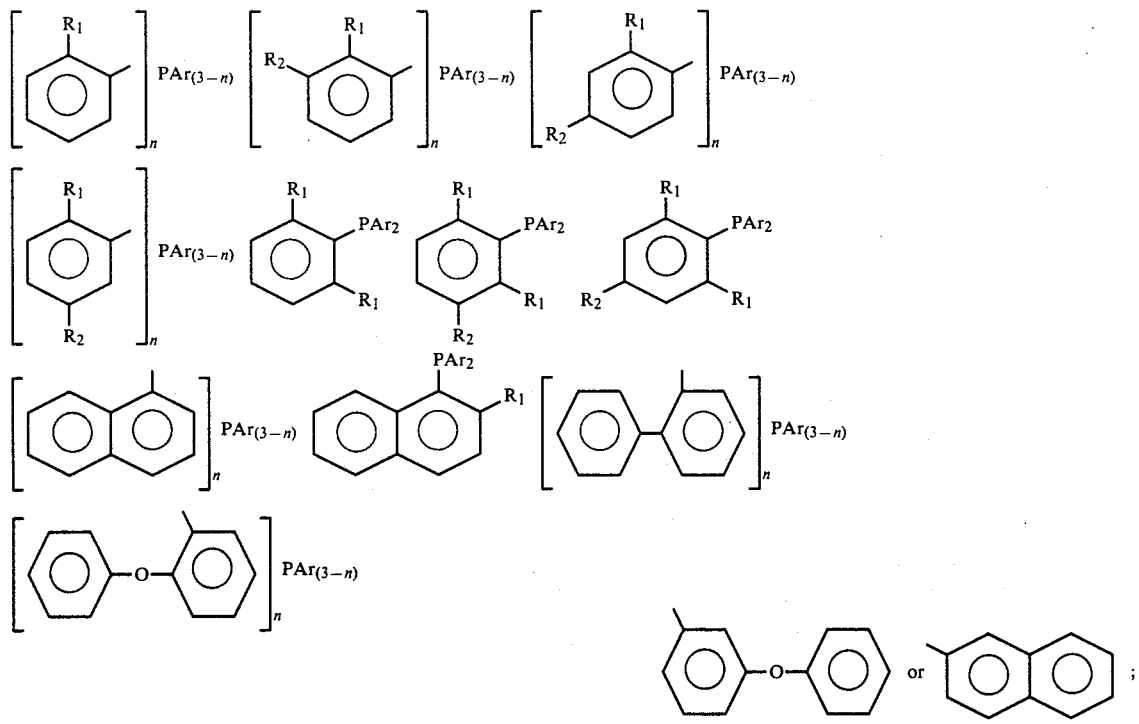

in which n=1 or 2 and wherein Ar is

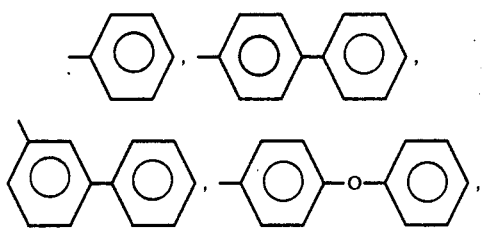

$R_1$ is selected from the group consisting of alkyl of 1-4 carbon atoms, alkoxy, and phenyl; and $R_2$ is selected from the group consisting of alkyl of 1-4 carbon atoms, alkoxy, chloride, fluoride, hydroxyl and carboxyl.

3. A process of claim 1 wherein the catalyst is present in amounts to provide about from 1 to $1 \times 10^{-5}$ moles of palladium per mole of propylene in the reaction mixture.

4. A process of claim 1 wherein the ortho-substituted ligand consists essentially of ortho-tolyl diphenylphosphine.

5. A process of claim 1 wherein the ortho-substituted ligand consists essentially of bis(o-tolyl)phenylphosphine.

* * * * *